United States Patent [19]

Black

[11] Patent Number: 4,885,096
[45] Date of Patent: Dec. 5, 1989

[54] AROMATICS - NON-ARMOATICS SEPARATION BY PERMEATION THROUGH THERMALLY CROSSLINKED NITRILE RUBBER MEMBRANES

[75] Inventor: Laura E. Black, Sarnia, Canada

[73] Assignee: Exxon Research and Engineering Company, Florham Park, N.J.

[21] Appl. No.: 205,720

[22] Filed: Jun. 13, 1988

[51] Int. Cl.$^4$ .............................................. B01D 13/00
[52] U.S. Cl. ................................. 210/640; 210/500.36; 210/500.43
[58] Field of Search .................... 210/640, 651, 500.22, 210/500.27, 500.36, 500.43

[56] References Cited

U.S. PATENT DOCUMENTS

| | | | |
|---|---|---|---|
| 2,947,687 | 8/1960 | Lee | 210/23 |
| 2,958,656 | 11/1960 | Stuckey | 210/23 |
| 2,958,657 | 11/1960 | Benning et al. | 210/23 |
| 2,970,106 | 1/1961 | Benning et al. | 208/347 |
| 3,043,891 | 7/1962 | Stuckey | 260/674 |
| 3,813,354 | 5/1974 | Chiolle et al. | 260/2.2 |
| 3,930,990 | 1/1976 | Brun et al. | 208/306 |

OTHER PUBLICATIONS

"Separation of Benzene-n Heptane Mixtures by Pervaporation with Elastomeric Membranes. I. Performance of Membranes", Larchet, et al., Journal of Membrane Society 15 (1983) 81–96.

Chemie Macromoleculaire, Brun, et al., C.R. Hebd. Frances Acad. Sci. Ser. C. 1977, 284 (20) 829-831.

*Primary Examiner*—Frank Spear
*Attorney, Agent, or Firm*—Joseph J. Allocca

[57] ABSTRACT

Aromatic hydrocarbons are separated from mixtures of same with non-aromatics by permeation through a membrane of thermally crosslinked polyconjugated diene rubber containing from 15 to 50 wt % nitrile groups. Thermal crosslinking increases selectivity far beyond the level obtained when crosslinking is caused by other techniques. The separations are conducted under pervaporation or perstraction conditions.

8 Claims, No Drawings

AROMATICS - NON-ARMOATICS SEPARATION BY PERMEATION THROUGH THERMALLY CROSSLINKED NITRILE RUBBER MEMBRANES

BRIEF DESCRIPTION OF THE INVENTION

Aromatic hydrocarbons are separated from mixtures of same with non-aromatics by permeation through a membrane of thermally crosslinked polyconjugated diene rubber containing from 15 to 50 wt % C≡N groups. A thin film of nitrile rubber is prepared using a casting solution containing 1 to 25 wt %, preferably 2 to 20 wt %, most preferably 5 to 18 wt % of the rubber in a dissolving solvent, spreading the casting solution on a suitable substrate for support, permitting the solvent to evaporate and crosslinking the polymer by exposing it to elevated temperatures in the range 140° to 200° C., preferably 160° to 180° C. for from 1 to 12 hours, preferably 3 to 9 hours. This thermal crosslinking is conducted in the absence of any catalyst such as peroxides. The separation is conducted using these membranes under pervaporation or perstraction conditions, preferably pervaporation conditions.

BACKGROUND OF THE INVENTION

The separation of aromatics from non-aromatics is a procedure of importance in the chemical and petroleum industry. Many techniques have been investigated and developed to perform the separation. Distillation under atmospheric or vacuum conditions has been employed when there is a sufficient difference in boiling point in the components to be separated. Alternatively extractive distillation or azeotropic distillation can be practiced. For mixtures of materials having little or no boiling point differentials, more sophisticated techniques must be employed, such as extraction using phenol, furfural, N-methyl pyrrolidone, sulfolane, glycols, $SO_2$ etc. as extraction solvents, or adsorption using natural or synthetic molecular sieves (zeolites). All of these techniques are either energy intensive or require a multitude of steps (e.g. separation of the aromatics from the extraction solvents, or desorption of aromatics from the adsorbents).

Other separation techniques have been investigated. The separation of aromatics from non-aromatics by permeation through selective membranes has received significant attention in the patent literature. Various membranes have been suggested for the separation. They include various cellulose esters, cellulose ethers, mixtures of cellulose esters and ethers, polyurethanes, polyethylene, polypropylene, polyvinylidine fluoride, and polyethylene styrene copolymers.

"Separation of benzene - n Heptane Mixtures By Pervaporation with Elastomeric Membranes, (I.) Performance of Membranes" Lorchet et al., Journal of Membrane Science 15 (1983) 81-96, shows aromatic/saturate separation by pervaporation through nitrile rubber or polybutadiene acrylonitrile membranes. The nitrile membranes were lightly crosslinked with from 0.5 to 6.0% dicumyl peroxide at 160°C. for 10 to 20 minutes. The article at pages 89 and 90 shows that varying the peroxide content from 0.5 to 6% did not appreciably change the performance of the membranes.

THE PRESENT INVENTION

It has been discovered that aromatic hydrocarbons can be separated from mixtures of same with non-aromatics by permeation of the aromatics through a thermally crosslinked nitrile rubber containing from 15 to 50 wt % nitrile groups.

The membrane is a polydiene polymeric material containing 15-50 wt % nitrile groups. Typical nitrile rubbers are copolymers of butadiene and acrylonitrile, but other dienes, preferably polyconjugated dienes, such as isoprene can also be polymerized with acrylonitrile or other nitrile moiety containing monomers to produce a useable polymeric material. All such polymers are hereinafter identified as nitrile rubbers for the sake of simplicity.

From 1 to 25 wt %, preferably 2 to 20 wt %, most preferably 5 to 18 wt % of the nitrile rubber is dissolved in a suitable solvent such as chlorobenzene, chloroform, 1,2 dichloroethane, dichloromethane, dimethylformamide, methyl ethyl ketone, n-methyl pyrollidone, ethyl acetate, tetrahydrofuron, etc. to form a casting solution. The solution is spread as a thin film on a suitable substrate like metal, glass, or woven fabric like teflon or other fabric which is not attached by either the polymer or its dissolving solvent. The solvent is permitted to evaporate from the film producing a symmetric film.

The membranes used in the present separation are cast without any catalytic crosslinking agent being present in the polymer casting solution.

The membranes are crosslinked using heat exclusively. The membranes are heated at a temperature of about 140° to about 200 °C., preferably 160° to 180° C., for from about 1 to 12 hours, preferably 3 to 9 hours.

Heat treatment causes a degree of crosslinking which is unattainable using catalytic crosslinking agents such as dicumyl peroxide, even when high concentrations of such catalysts are employed.

Furthermore, heat treatment when no catalyst is present produces a membrane which has a higher selectivity factor than that obtained when heat treatment is practiced on a membrane in which a catalyst is present.

The separation process using the thermally crosslinked nitrile rubber membranes is preferably conducted under perstraction or pervaporation conditions.

In perstraction, the feed is contacted with one side of the selective membrane at a temperature in the range of about 20° to 200° C. The aromatic component selectively dissolves into the membrane and permeates through the membrane. Since this process is driven by the existence of a concentration gradient across the membrane it is necessary that the concentration of aromatics on the permeate side of the membrane be kept low. This is accomplished by use of a sweep liquid. The primary characteristic of the sweep liquid is the ease by which it can be separated from the swept aromatic.

Pervaporation is a more efficient separation process. It is conducted at an elevated temperature, a temperature high enough to provide the heat of vaporization of the aromatic component. The mixture feed is contacted with one side of the selective membrane. This contacting is at a temperature in the range 0° to 200° C. and an applied pressure of 0 to 1000 psig. The aromatic selectively dissolves into the membrane and migrates to the permeate side. As in perstraction, pervaporation is driven by the existence of a concentration gradient. In the case of pervaporation this gradient is maintained by applying a vacuum or passing a sweep gas on the permeate side of the membrane to draw away the permeated aromatic hydrocarbon. Vacuum drawn on the permeate side is such that the pressure is less than the equilibrium vapor pressure of the liquid feed. Vacuums on the order of 0.1 to 50 mm Hg are typical at the temperatures employed.

The process is used in the petroleum industry to separate aromatic hydrocarbons from mixtures of aromatic hydrocarbons and non-aromatic hydrocarbons. Typical non-limiting examples of feeds which are or contain mixtures of aromatic and non-aromatic hydrocarbons are naphtha, catalytic naphtha, gas oils, heavy cat naphtha, light gas oils, light cat. gas oils, etc. The separation process can also be used in the chemical industry for recovery/concentration of aromatics such as benzene, toluene, xylenes, etc. from chemical process streams.

The invention is illustrated in detail by reference to the following non-limiting examples and comparisons.

EXAMPLE 1

This example discusses the effect of crosslinking time and temperature on the performance of membranes containing 20% dicumyl peroxide and explains why thermal crosslinking, not the peroxide content, is the determining factor in preparing high selectivity nitrile rubber membranes.

The polymer solution was prepared by co-dissolving nitrile rubber (45 wt % acrylonitrile content) and dicumyl peroxide in chlorobenzene. The total solids in solution were kept constant at 18 wt %. The solutions were cast on porous $0.2\mu$ teflon membranes. The films were dried and then heated at various temperatures ($>135°$ C.) for various periods of time ($>1$ hour) in a vacuum oven under a nitrogen purge. The membrane thickness varied from 50 to 80 microns. These membranes were tested under pervaporation conditions using an 80/20 benzene/cyclohexane feed at 28° C. with the downstream pressure maintained at 1 mbar. The results are listed in Table 1.

Initially, these membranes were cured at 137° C. for 1 and 2 hours. These membranes demonstrated selectivity factors of 3.06 to 3.15 at permeability values of 750 and 870 kgu/m² day. According to literature documentating the use of dicumyl peroxide with nitrile rubber (Hercules Technical Data bulletins ORC-105B, ORC-201C, ORC-101B) at 137° C., an appreciable amount of peroxide would be undecomposed even after 2 hours.

According to the literature, at a cure temperature of 160° C., a cure time of 1 hour would result in more than 99% of the peroxide decomposing. The selectivity factor for a membrane treated under this condition was only slightly higher at 3.31 which is close to the value of 3.5 observed in literature. From this result, it is shown that membranes with a high dicumyl peroxide content of 20% do not show any higher selectivities than the literature membranes containing 0.5 to 5% dicumyl peroxide.

Surprisingly, membranes treated at 160° C. for 3 and 9 hours showed significantly higher selectivity factors of 3.84 and 4.43 and reduced permeability values of 530 and 360 kgu/m² day. This increased selectivity and reduced permeability cannot be attributed to peroxide catalyzed crosslinking as all of the peroxide would have been decomposed after 1 hour. It is known (Rubber Chemistry and Technology 31 (1958) 132-146) that nitrile rubber can thermally crosslink at an elevated temperature of 180° C. The increased selectivity at longer treatment times is attributed to thermal crosslinking. The degree of thermal crosslinking would continually increase as the cure time is increased.

EXAMPLE 2

This example discusses the effect of the dicumyl peroxide content on the performance of thermally crosslinked nitrile rubber membranes and shows that no peroxide is required to achieve high selectivity thermally crosslinked nitrile rubber membranes.

The membranes were prepared and tested as detailed in Example 1. The results are listed in Table 2.

As shown for membranes heat treated at 160° C. for 9 hours, the selectivity factor increased as the dicumyl peroxide content decreased. For membranes containing 20, 15, 10, and 5% dicumyl peroxide at 28° C., the selectivity factors increased from 4.43 to 5.8 and the permeability values stayed relatively constant ranging mostly between 330 and 390 kgu/m² day.

A membrane containing no dicumyl peroxide heat treated at 165° C. for 2.5 hours, was also tested and showed a selectivity factor of 5.4 with a permeability value of 320 kgu/m² day. This selectivity factor is significantly higher than that of the literature membranes at a selectivity factor of 3.5.

Clearly, no dicumyl peroxide is required in preparing high selectivity membranes. The selectivity and permeability of nitrile rubber membranes can be controlled by the degree of thermal crosslinking that they undergo.

TABLE 1

PERFORMANCE OF CAST NITRILE RUBBER MEMBRANES
CONTAINING 20% DICUMYL PEROXIDE
Wt % ACN in polymer = 45
Feed = 80/20 benzene/cyclohexane
Feed temperature = 28.2° C.

| Temperature of Cure °C. | Time of Cure (hr) | Membrane (1) Thickness (μ) | % Benzene Permeate | Selectivity Factor | Permeability Value kg /m²day (2) |
|---|---|---|---|---|---|
| 137 | 1 | 50 | 92.4 | 3.06 | 750 |
| 137 | 2 | 50 | 92.6 | 3.15 | 870 |
| 160 | 1 | 48 | 93.0 | 3.31 | 750 |
| 162 | 3 | 53 | 93.9 | 3.84 | 530 |
| 160 | 9 | 50 | 94.7 | 4.43 | 360 |

(1) Measured by micrometer.
(2) Using membrane thickness as measured by micrometer. Permeability value is product of flux and membrane thickness and represents the permeate flux estimated for a membrane 1μ thick (assuming flux is inversely proportional to thickness).

TABLE 2

PERFORMANCE OF MEMBRANE WITH DIFFERENT CONCENTRATIONS OF DICUMYL PEROXIDE
Wt % ACN in polymer = 45
Feed = 80/20 benzene/cyclohexane

| Temperature of Cure °C. | Time of Cure (hr) | % Dicumyl Peroxide | Temperature of Feed °C. | Membrane Thickness (μ) | % Benzene Permeate | Selectivity Factor | Permeability Value kg/m²day (2) |
|---|---|---|---|---|---|---|---|
| 160 | 9 | 20 | 28 | 50 | 94.7 | 4.5 | 360 |
|  |  | 15 | 28 | 45 | 95.2 | 5.0 | 570 |
|  |  | 10 | 28 | 55 | 95.7 | 5.6 | 360 |
|  |  | 5 | 28 | 58 | 95.9 | 5.8 | 330 |
| 165 | 2.5 | 0 | 28 | 80 | 95.6 | 5.4 | 320 |

(1) Measured by micrometer.
(2) Using membrane thickness as measured by micrometer. Permeability value is product of flux and membrane thickness and represents the premeate flux estimated for a membrane 1μ thick (assuming flux is inversely proportional to thickness).

What is claimed is:

1. A method for separating aromatic hydrocarbons from mixtures containing aromatic hydrocarbons and non-aromatic hydrocarbons, the method comprising selectively permeating the aromatic hydrocarbon through a membrane of polyconjugated diene rubber containing from 15 to 50 wt % nitrile groups said membrane being thermally crosslinked in the absence of any catalytic crosslinking agent.

2. The method of claim 1 wherein the aromatic hydrocarbon permeation is conducted under pervaporation conditions.

3. The method of claim 1 wherein the aromatic hydrocarbon permeation is conducted under perstraction conditions.

4. The method of claim 1 wherein the membrane comprises a thermally crosslinked copolymer of butadiene and acrylonitrile.

5. The method of claim 1 or 4 wherein the thermal crosslinking is performed by heating the membrane at a temperature of about 140° to 200° C. for from about 1 to 12 hours.

6. The method of claim 5 wherein the thermal crosslinking is performed by heating the membrane at a temperature of about 160° to 180° C.

7. The method of claim 5 wherein the heating is conducted for from 3 to 9 hours.

8. The method of claim 6 wherein the heating is conducted for from 3 to 9 hours.

* * * * *